United States Patent [19]

Moore

[11] Patent Number: Plant 7,617

[45] Date of Patent: Aug. 13, 1991

[54] MINIATURE ROSE PLANT NAMED 'MORART'

[76] Inventor: Ralph S. Moore, 2519 E. Noble Ave., Visalia, Calif. 93277

[21] Appl. No.: 462,480

[22] Filed: Jan. 8, 1990

[51] Int. Cl.[5] ..... A01H 5/00

[52] U.S. Cl. ..... Plt./4

[58] Field of Search ..... Plt. 2, 3, 4, 5, 6, Plt./7

*Primary Examiner*—James R. Feyrer

[57] ABSTRACT

The subject of the present disclosure is a new and distinct variety of climbing miniature rose plant characterized by buds and flowers of good substance and of a color blending orange and yellow.

1 Drawing Sheet

1

The present invention relates to a new and distinct variety of hardy, climbing type rose plant of the miniature class; the variety being primarily characterized — as to novelty — by orange buds and flowers. The general color effect being orange.

The variety is further characterized by:

An abundance of bloom, with flowers, on mature plant, usually borne several together in loose spray or cluster.

Fruity fragrance.

A plant which is vigorous, of upright, climbing habit with semi-glossy to matt, medium foliage with pointed leaflets; the buds and flowers being similar in form and color to Mary Marshall (Miniature — U.S. Plant Pat. No. 3,346) but slightly larger.

The plant, which has a normal height of about 6 feet or more, can easily be maintained at lesser height by occasional trimming.

A plant which grows and blooms satisfactorily both in greenhouse and outdoors; is good for growing in large pots or garden and provides excellent garden decoration as well as cut flowers.

The present variety of miniature rose was originated by me at Sequoia Nursery, located at Visalia, Calif. under conditions of careful control and observation, as a cross between #1-72-1 (Little Darling×Yellow Magic), un-named, climbing miniature, as the seed parent and Gold Badge (Var: Meigronuri) Floribunda — U.S. Plant Pat. No. 4,625 — as the pollen parent.

Subsequent to origination of the variety I successfully reproduced it, at Sequoia Nursery, located as aforesaid, by budding as well as by cuttings; the reproductions having run true in all respects.

The color photograph illustrates the variety, including buds and flowers.

Referring now specifically to the new and distinct variety of miniature rose plant, the following is a detailed description thereof in outline; all major color plate identifications being by reference to the British Colour Council Horticultural Color Chart, except where common terms of color definition are employed.

Type: Hardy; rounded to upright; seedling; greenhouse; outdoors; cut flowers; garden decoration.

Class: Climbing miniature.

*International identification.*—Variety; Morart.

*Commercial synonym.*—Work Of Art.

Flowers borne: Usually borne in loose sprays of 3 to 7 or more on slender wirey stems.

2

Quantity of bloom: Abundant both outside and in greenhouse.

Bud:

*Peduncle.*—Fairly long; slender but sturdy; erect; medium green, sometimes lightly tinted bronze (outdoors).

*Hairs.*—Usually quite smooth. Before calyx breaks; size — small. Form.—Long; pointed with several small foliaceous apendages on surface of bud; with foliaceous parts extending beyond the tip of the bud equal to more than one half of its length.

*Color.*—Medium green, occasionally tinted with bronze. (outdoors). As calyx breaks, color — reddish. Openings: Opens well in all weather.

Bloom:

*Size when fully open.*—Small, averaging about 40-50 mm (2").

*Petalage.*—Double — averaging about 35 petals arranged regularly with occasionally 2 or 3 small petaloids.

*Form.*—High centered then becoming more rounded with petals reflexing loosely outward. Open flowers may show stamens.

Petals: Fairly thick; satiny on inside and on outside surface.

*Shape.*—Outside petals, broad lanceolate; rounded with very short acute tip; intermediate — broad lanceolate with short acute tip; inside — lanceolate with short acute tip.

Color: Newly opened flower from a plant grown in plastic greenhouse (Nov., 1988), Visalia, Calif.

*Outside petal.*—Outside surface — dull orange (near Brick Red 016/1 and/or Burnt Orange 014/1 with yellowish areas) with darker veining and small yellowish area at base. Inside surface — near Brick Red 016, suffused with yellow and blending into bright yellow at base.

*Intermediate petal.*—Outside surface similar to outside petal. Inside surface similar to outside petal.

*Inner petal.*—Outside surface similar to intermediate petal. Inside surface — similar to intermediate petal. General color effect; newly opened flowers — orange. Three days open — color similar but lighter (more pinkish). Note: The blending of colors, orange, yellow and pink can vary according to season of year, light intensity, etc. Thus flowers may be slightly lighter or darker than described or illustrated.

Behavior: Opens well in all weather. Spent petals drop off.

*Flower longevity* (*Sep.* 1989).—Plant in large pot 5–6 days or longer. Cut flowers at living room temperature 4–6 days.

Reproductive organs:

*Stamens.*—Numerous, arranged regularly about pistils.

*Filaments.*—Varying length, medium long, yellow.

*Anthers.*—Yellow.

*Pollen.*—Moderate amount.

*Pistils.*—Average number.

*Styles.*—Fairly even; medium length; bunched; color — yellowish.

*Ovaries.*—All enclosed in calyx.

*Hips.*—Some, ball shaped, orange.

*Sepals.*—Permanent; spear shaped; recurved against peduncle.

*Seed.*—Few to several.

Foliage:

*Leaves.*—Compound of five (sometimes three of seven) leaflets; fairly small; leathery; semi-glossy to matt.

*Leaflets.*—Shape: broad, lanceolate; apex acute; base rounded (sometimes acute). Margin serrate.

*Color.*—Medium green; new growth — normal (medium) green.

*Rachis.*—Medium strength; upperside may have a few very tiny short hairs, grooved; underside smooth with few or no tiny prickles (usually none).

*Stipules.*—Short to medium length; narrow to medium width; rather long; narrow points which turn out usually at about 45 degrees or more.

Growth:

*Habit.*—Bushy; upright; much branched.

*Growth.*—Free vigorous; internodes short.

*Canes.*—Medium slender; sturdy.

*Main stems.*—Color — medium green.

*Thorns.*—Few to none; prickles — none.

*Branches.*—Color: medium green. Thorns: few to none. Prickles: none. Hairs; none.

The miniature plant and its flowers as herein described may vary in slight detail due to climatic, soil and cultural conditions under which the variety may be grown; the present description being of the variety as grown at Visalia, Calif.

The following is claimed:

1. A new and distinct variety of climbing miniature rose plant of hardy, bushy, to upright, much branched habit substantially as illustrated and described, characterized by buds and flowers which are orange blended with yellow, sometimes tending to be more pink blended with yellow; the bud and flower resembling the variety Mary Marshall (Miniature — U.S. Plant Pat. No. 3,346) in form and color; and further characterized by a plant of vigorous and upright growth habit, easy to propagate from cuttings or by budding, with an abundance of medium size semi-glossy to matt foliage, and an abundance of flowers usually borne in loose cluster of 3 to 7 or more.

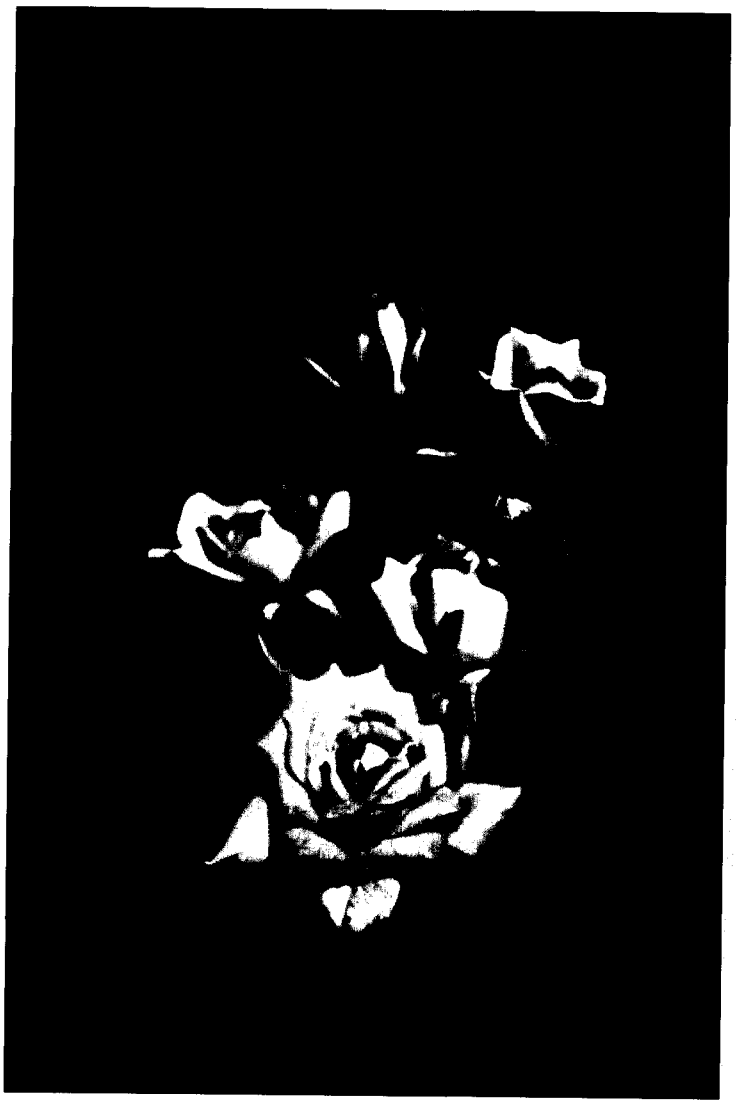

* * * * *